United States Patent
Brake et al.

(10) Patent No.: US 10,603,260 B2
(45) Date of Patent: Mar. 31, 2020

(54) STORAGE-STABLE DEVELOPER FOR OXIDATIVE DYE

(71) Applicant: Henkel AG & Co. KGaA, Duesseldorf (DE)

(72) Inventors: Carsten Brake, Essen (DE); Burkhard Mueller, Duesseldorf (DE); Torsten Lechner, Langenfeld (DE); Lucile Bonnin, Duesseldorf (DE); Laura Knechtel, Ebringen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/174,610

(22) Filed: Oct. 30, 2018

(65) Prior Publication Data

US 2019/0142717 A1    May 16, 2019

(30) Foreign Application Priority Data

Nov. 16, 2017 (DE) .......................... 10 2017 220 439

(51) Int. Cl.
| | |
|---|---|
| *A61Q 5/10* | (2006.01) |
| *A61K 8/22* | (2006.01) |
| *A61K 8/19* | (2006.01) |
| *A61K 8/24* | (2006.01) |
| *A61K 8/34* | (2006.01) |
| *A61K 8/368* | (2006.01) |
| *A61K 8/46* | (2006.01) |
| *A61K 8/49* | (2006.01) |
| *A61K 8/55* | (2006.01) |
| *A61K 8/73* | (2006.01) |

(52) U.S. Cl.
CPC ................. *A61K 8/22* (2013.01); *A61K 8/19* (2013.01); *A61K 8/24* (2013.01); *A61K 8/342* (2013.01); *A61K 8/368* (2013.01); *A61K 8/463* (2013.01); *A61K 8/4926* (2013.01); *A61K 8/55* (2013.01); *A61K 8/73* (2013.01); *A61Q 5/10* (2013.01); *A61K 2800/30* (2013.01); *A61K 2800/43* (2013.01); *A61K 2800/882* (2013.01)

(58) Field of Classification Search
CPC ........ A61Q 5/10; A61K 8/411; A61K 8/4926; A61K 8/22; A61K 8/19; A61K 8/342; A61K 2800/88; A61K 2800/882; A61K 8/34; A61K 8/463; A61K 8/73; A61K 8/361; A61K 8/24; A61K 8/55
See application file for complete search history.

(56) References Cited

U.S. PATENT DOCUMENTS

| | | | |
|---|---|---|---|
| 8,740,995 B1 * | 6/2014 | Schweinsberg | A61K 8/4926 132/202 |
| 2014/0166035 A1 * | 6/2014 | Babiel | A61K 8/37 132/208 |
| 2016/0271031 A1 * | 9/2016 | Schweinsberg | A61K 8/416 |
| 2017/0165161 A1 | 6/2017 | Manneck et al. | |

FOREIGN PATENT DOCUMENTS

DE        19756454.2 C1    6/1999

* cited by examiner

*Primary Examiner* — Eisa B Elhilo

(74) *Attorney, Agent, or Firm* — Lorenz & Kopf, LLP

(57) ABSTRACT

Oxidative compositions for oxidative treatment of hair, kits including such compositions, and methods for oxidative color change are provided. An exemplary oxidative composition includes comprises water, hydrogen peroxide, at least linear saturated 1-alkanol with from about 12 to about 30 carbon atoms, at least one anionic surfactant selected from alkyl sulfates and alkyl ether sulfates, dipicolinic acid, 1-hydroxyethane-1,1-diphosphonic acid, disodium pyrophosphate, benzoic acid or a salt thereof, and potassium hydroxide. The exemplary oxidative composition has a pH in the range of from about 2 to about 3.8, each measured at 20° C. The exemplary oxidative composition includes no phosphoric acid, no salicylic acid, no diethylenetriamine pentaacetic acid, no ethylenediamine tetraacetic acid, no nitrilotriacetic acid nor salts thereof, and no phenacetin, no stannates, no cationic surfactants and no oil.

9 Claims, No Drawings

STORAGE-STABLE DEVELOPER FOR OXIDATIVE DYE

CROSS-REFERENCE TO RELATED APPLICATION

This application claims priority to German Patent Application No. 10 2017 220 439.7, filed Nov. 16, 2017, which is incorporated herein by reference in its entirety.

TECHNICAL FIELD

The present application relates to compositions suitable for hair lighteners and/or hair dye preparations, in particular for hair lighteners and/or hair dye creams containing fatty alcohol, wherein the hair lightener and/or hair dye preparations contain ammonia and/or ammonium hydroxide and/or monoethanolamine as alkalizing agents and optionally at least one oxidative dye precursor and have a pH in the range of from about 8 to about 11.5, measured at about 20° C.

BACKGROUND

The oxidative compositions as contemplated herein have an improved stability in storage of the emulsion as well as an improved stability in storage of the pH and thus of the hydrogen peroxide so that color development of the application mixture still corresponds to the product specification even if the oxidative composition has been stored for a longer period of time. The improved storage stability is manifested in particular at extreme temperatures of from about −10° C. and about +40° C.

Another subject matter of the present application relates to agents for changing the color of keratinic fibers that can be produced from two separate compositions by mixing the two compositions, wherein one of the two compositions is an oxidative composition according to the first subject matter of the application and the second composition is a hair lightener and/or hair dye preparation, in particular a hair lightener and/or hair dye cream containing fatty alcohol and also containing ammonia and/or monoethanolamine as the alkalizing agent and optionally at least one oxidative dye precursor and having a pH in the range of from about 8 to about 11.5, measured at about 20° C. and also preferably each based on the weight of the second alkaline composition, from about 25 to about 90 wt % preferably from about 65 to about 85 wt % water, additionally at least one 1-alkanol with from about 10 to about 30 carbon atoms, which is linear or branched and saturated or unsaturated and is preferably selected from lauryl alcohol, myristyl alcohol, cetyl alcohol, stearyl alcohol, arachidyl alcohol, 2-octyldodecan-1-ol and behenyl alcohol as well as mixtures of these 1-alkanols, especially preferably cetyl alcohol, stearyl alcohol, arachidyl alcohol, behenyl alcohol and cetyl alcohol/stearyl alcohol mixtures in a total amount of from about 2 to about 20 wt %, preferably from about 2.5 to about 16 wt %, additionally at least one surfactant in a total amount of from about 0.1 to about 7 wt %, preferably from about 1.8 to about 4 wt % and optionally additional ingredients such as organic solvents, chelating agents, antioxidants and/or reducing agents (to improve the storage stability of the oxidative dye precursors) polymers, oils, silicones and perfumes. The term "surfactant" also comprises within the scope of the present application, emulsifiers but not the 1-alkanols with from about 10 to about 30 carbon atoms listed above.

Another subject matter of the present application relates to a kit for oxidative color change of keratinic fibers, comprising an alkalizing preparation, which optionally contains dye, ammonia and/or monoethanolamine and a hydrogen peroxide preparation according to the present disclosure or preferred according to the present disclosure, wherein the hydrogen peroxide preparation is optimized, so that the ready-to-use mixture including of about 1 part by weight alkalizing preparation and from about 0.5 to about 4 parts by weight, preferably from about 1 to about 3 parts by weight, especially preferably from about 1 to about 2 parts by weight hydrogen peroxide preparation, is a viscous cream or paste with a viscosity in the range of from about 2000 to about 5000 mPas (for example, measured at about 20° C. with a Haake viscometer model MV2 at a speed of about 8 rpm), which can be applied well to fibers that are to be dyed and/or brightened and remains on the hair during the treatment time of from about 1 to about 60 minutes, preferably from about 10 to about 45 minutes, especially preferably from about 20 to about 30 minutes, without dripping off the hair to any significant extent.

Another subject matter of the present disclosure relates to a method for oxidative color change of keratinic fibers, wherein the ready-to-use lightener and/or dye is prepared by mixing the components of the aforementioned kit immediately before use, then applying the mixture to the fibers, in particular hair, and then rinsing it off after a treatment time of from about 1 to about 60 minutes, preferably from about 10 to about 45 minutes, especially preferably from about 20 to about 30 minutes.

BRIEF SUMMARY

Oxidative compositions for oxidative treatment of hair, kits including such compositions, and methods for oxidative color change are provided. An exemplary oxidative composition includes water, hydrogen peroxide, at least linear saturated 1-alkanol with from about 12 to about 30 carbon atoms, at least one anionic surfactant selected from alkyl sulfates and alkyl ether sulfates, dipicolinic acid, 1-hydroxyethane-1,1-diphosphonic acid, disodium pyrophosphate, benzoic acid or a salt thereof, and potassium hydroxide. The exemplary oxidative composition has a pH in the range of from about 2 to about 3.8, each measured at 20° C. The exemplary oxidative composition includes no phosphoric acid, no salicylic acid, no diethylenetriamine pentaacetic acid, no ethylenediamine tetraacetic acid, no nitrilotriacetic acid nor salts thereof, and no phenacetin, no stannates, no cationic surfactants and no oil.

An exemplary kit for oxidative color change of keratinic fibers includes two separate compositions (A) and (B). Composition (B) is an oxidative composition including water, hydrogen peroxide, at least linear saturated 1-alkanol with from about 12 to about 30 carbon atoms, at least one anionic surfactant selected from alkyl sulfates and alkyl ether sulfates, dipicolinic acid, 1-hydroxyethane-1,1-diphosphonic acid, disodium pyrophosphate, benzoic acid or a salt thereof, and potassium hydroxide. The exemplary composition (B) has a pH in the range of from about 2 to about 3.8, each measured at 20° C. The exemplary composition (B) includes no phosphoric acid, no salicylic acid, no diethylenetriamine pentaacetic acid, no ethylenediamine tetraacetic acid, no nitrilotriacetic acid nor salts thereof, and no phenacetin, no stannates, no cationic surfactants and no oil. Composition (A) includes water, ammonia and/or monoethanolamine, at least one 1-alkanol with from about 10 to about 30 carbon atoms which is linear or branched and saturated or unsaturated, at least one surfactant, optionally additional ingredients selected from organic solvents, chelating agents, antioxidants and/or reducing agents, polymers, oils, silicones and perfumes, and optionally at least one oxidative dye precursor. An exemplary composition (A) has a pH in the range of from about 8 to about 11.5, measured at 20° C. Compositions (A) and (B) may be provided in a weight ratio A/B of from about ⅓ to about ¾.

An exemplary method for oxidative color change of keratinic fibers includes providing an oxidative composition (B) including water, hydrogen peroxide, at least linear saturated 1-alkanol with from about 12 to about 30 carbon atoms, at least one anionic surfactant selected from alkyl sulfates and alkyl ether sulfates, each with from about 10 to about 20 carbon atoms in the alkyl group and from about 0 to about 16 glycol ether groups in the molecule, dipicolinic acid, 1-hydroxyethane-1,1-diphosphonic acid, disodium pyrophosphate, benzoic acid or a salt thereof, and potassium hydroxide. The exemplary oxidative composition (B) has a pH in the range of from about 2 to about 3.8, each measured at 20° C. The exemplary oxidative composition (B) comprises no phosphoric acid, no salicylic acid, no diethylenetriamine pentaacetic acid, no ethylenediamine tetraacetic acid, no nitrilotriacetic acid nor salts thereof, and no phenacetin, no stannates, no cationic surfactants, and no oil. The method further includes providing a composition (A) including water, ammonia and/or monoethanolamine, at least one 1-alkanol with from about 10 to about 30 carbon atoms which is linear or branched and saturated or unsaturated, at least one surfactant, optionally additional ingredients selected from organic solvents, chelating agents, antioxidants and/or reducing agents, polymers, oils, silicones, and perfumes, and optionally at least one oxidative dye precursor. An exemplary composition (A) has a pH in the range of from about 8 to about 11.5, measured at 20° C. The method further includes mixing the oxidative composition (B) and the composition (A) in a weight-based mixing ratio A/B of from about $^{0.33}/_1$ to about ¾ to from a ready-to-use composition, immediately thereafter distributing the ready-to-use composition on the fibers, leaving the composition on the fibers for a period of from about 1 to about 60 minutes, and immediately thereafter rinsing the remaining ready-to-use composition out of the fibers and optionally drying the fibers.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure relates to oxidative color change of keratinic fibers, in particular hair. When treating keratinic fibers, in particular hair, with oxidative agents, in particular with hydrogen peroxide, the pigment melanine, which is endogenous in the fibers, is destroyed to a certain extent, so that the hair is or the fibers are necessarily lightened, so that their color changes even in the absence of a dye. Therefore, the term "color change" in the sense of the present patent application covers both lightening and dyeing with one or more dyes.

Those skilled in the art are familiar with various methods for changing the color of human hair. In general, either direct dyes or oxidative dyes are used for dyeing human hair. Oxidative dyes are formed by oxidative coupling of one or more developer components with one another or with one or more coupler components. Coupler components and developer components are also referred to as oxidative dye precursors. Dyeings achieved with oxidative dyes are usually referred to as permanent or semipermanent dyeings.

These agents usually contain hydrogen peroxide as the oxidative agent. Since hydrogen peroxide has inadequate stability in storage in an alkaline pH range, oxidative dyes usually consist of two components that are mixed together immediately prior to use. One component contains hydrogen peroxide in an aqueous solution or emulsion, wherein this composition has an acidic pH, usually in the range of from about 2.5 to about 5.5, to stabilize the hydrogen peroxide. The second component contains one or more alkalizing agents in an amount such that the application mixture of the two components has a pH in the range of from about 8 to about 11. If the alkalizing preparation does not contain any dye or contains only small amounts of dye—the latter serves to conceal unwanted colors that can occur in oxidation of melanine—then it is a lightener or bleaching agent. However, the alkalizing preparation may also contain oxidative dye precursors and/or direct dyes and then the resulting application mixture serves as a dyeing agent. In addition, there are also dye kits and dyeing methods in which the application mixture of the two components has a pH in the range of approx. 6 to about 7.9. However, the dye results with these so-called "acidic" dyeings often do not achieve the quality associated with alkaline application mixtures.

In addition, the alkalizing preparations contain ammonia and/or monoethanolamine as the alkalizing agent and optionally at least one oxidative dye precursor, and they have a pH in the range of from about 8 to about 11.5 measured at about 20° C.

In addition, the preferred alkalizing preparations are those that contain, each based on its weight, from about 25 to about 90 wt %, preferably from about 65 to about 85 wt % water, also at least one 1-alkanol with from about 10 to about 30 carbon atoms, which is linear or branched and saturated or unsaturated and is preferably selected from lauryl alcohol, myristyl alcohol, cetyl alcohol, stearyl alcohol, arachidyl alcohol, 2-octyldodecan-1-ol and behenyl alcohol as well as mixtures of these 1-alkanols, especially preferably cetyl alcohol, stearyl alcohol, arachidyl alcohol, behenyl alcohol and cetyl alcohol/stearyl alcohol mixtures, in a total amount of from about 2 to about 20 wt %, preferably from about 2.5 to about 16 wt %, additionally at least one surfactant in a total amount of from about 0.1 to about 7 wt %, preferably from about 1.8 to about 4 wt % and optionally additional ingredients such as organic solvents, chelating agents, antioxidants and/or reducing agents (to improve the stability in storage of the oxidative dye precursors), polymers, oils, silicones and perfumes and optionally at least one oxidative dye precursor product, wherein all the content data is based on the weight of the composition (A).

For oxidative change of hair color, the composition (A) is mixed with the aqueous oxidative agent preparation as contemplated herein, referred to as composition (B), wherein the compositions (A) and (B) are preferably present in a weight ratio A/B in the range of from about 0.33 to about 3, especially preferably from about 0.5 to about 2, extremely preferably about 1:1. Compositions (A) and (B) are mixed in a resealable bottle or a shaker container, for example, and the resulting application mixture is applied to the hair to be treated, where it remains for a treatment time of from about 1 to about 60 minutes, preferably from about 10 to about 45 minutes, especially preferably from about 20 to about 30 minutes, before being rinsed off.

The object of the present disclosure was to provide an oxidative dye preparation that is more stable in storage for oxidative color change agents that are available in the form hair lightener creams and/or hair dye creams containing fatty alcohol, wherein the hair lightener and/or hair dye preparations contains ammonia and/or ammonium hydroxide and/or monoethanolamine as alkalizing agents and optionally at least one oxidative dye precursor and have a pH in the range of from about 8 to about 11.5, measured at about 20° C., with which it is possible to prepare homogenous application mixtures with a stable viscosity.

It has surprisingly been found that aqueous hydrogen peroxide preparations containing selected 1-alkanols in a total amount of from about 1 to about 2.8 wt %, selected anionic surfactants in a total amount of from about 0.05 to about 0.5 wt %, also dipicolinic acid, 1-hydroxyethane-1,1-diphosphonic acid, disodium pyrophosphate, benzoic acid and potassium hydroxide in selected amounts can be adjusted to be stable in storage at a pH in the range of from about 2 to about 3.8 (20° C.) without the addition of further stabilizers and can solve the problems formulated here in a very good manner.

A first subject matter of the present disclosure is therefore an oxidative composition for oxidative treatment of hair, containing:
  from about 50 to about 97 wt % preferably from about 80 to about 95 wt %, especially preferably from about 85 to about 92 wt % water,
  from about 0.5 to about 20 wt % hydrogen peroxide,
  at least one linear, saturated 1-alkanol with from about 12 to about 30 carbon atoms in a total amount of from about 1 to about 2.8 wt %, preferably from about 1.2 to about 2.5 wt %, especially preferably from about 1.4 to about 1.7 wt %, additionally
  containing
  at least one anionic surfactant selected from alkyl sulfates and alkyl ether sulfates, each with from about 10 to about 20 carbon atoms in the alkyl group and from about 0 to about 16, preferably two to three glycol ether groups in the molecule in a total amount of from about 0.05 to about 0.5 wt %, preferably of from about 0.1 to about 0.4 wt %, especially preferably of from about 0.15 to about 3 wt %, extremely preferably from about 0.2 to about 0.25 wt %, additionally containing
  dipicolinic acid in an amount of from about 0.02 to about 0.2 wt %, preferably from about 0.03 to about 0.17 wt %, especially preferably from about 0.05 to about 0.13 wt %, extremely preferably from about 0.07 to about 0.1 wt %, additionally containing
  1-hydroxyethane-1,1-diphosphonic acid in an amount of from about 0.05 to about 0.5 wt %, preferably from about 0.1 to about 0.4 wt %, especially preferably from about 0.18 to about 0.25 wt %, additionally containing
  disodium pyrophosphate in an amount of from about 0.02 to about 0.2 wt %, preferably from about 0.05 to about 0.17 wt %, especially preferably from about 0.1 to about 0.13 wt %, additionally containing
  benzoic acid or a salt thereof in a total amount of from about 0.02 to about 0.06 wt %, preferably from about 0.03 to about 0.04 wt %, additionally containing
  potassium hydroxide in an amount of from about 0.025 to about 0.3 wt %, preferably from about 0.07 to about 0.15 wt %,
wherein the oxidative composition has a pH in the range of from about 2 to about 3.8, preferably in the range of from about 2.5 to about 3.5, especially preferably in the range of from about 2.8 to about 3.3, each measured at about 20° C., wherein the composition contains no phosphoric acid, no salicylic acid, no diethylenetriamine pentaacetic acid, no ethylenediamine tetraacetic acid, no nitrilotriacetic acid or salts of these acids and no phenacetin, no stannates, no cationic surfactants and no oil, and
wherein all the quantity data is based on the weight of the oxidative composition.

The oxidative composition as contemplated herein contains, each based on its weight, from about 50 to about 97 wt %, preferably from about 80 to about 95 wt %, especially preferably from about 85 to about 92 wt % water.

The oxidative composition as contemplated herein contains, each based on its weight, from about 0.5 to about 20 wt %, preferably from about 3 to about 12 wt %, especially preferably from about 6 to about 9 wt % hydrogen peroxide.

The oxidative composition as contemplated herein additionally contains at least one linear saturated 1-alkanol with from about 12 to about 30 carbon atoms in a total amount of from about 1 to about 2.8 wt %, preferably from about 1.2 to about 2.5 wt %, especially preferably from about 1.4 to about 1.7 wt %, each based on the weight of the oxidative composition.

The at least one linear saturated 1-alkanol with from about 12 to about 30 carbon atoms is preferably selected from lauryl alcohol, myristyl alcohol, cetyl alcohol, stearyl alcohol, arachidyl alcohol and behenyl alcohol as well as mixtures of these 1-alkanols, especially preferably cetyl alcohol, stearyl alcohol, arachidyl alcohol, behenyl alcohol and cetyl alcohol/stearyl alcohol mixtures. Preferred oxidative compositions as contemplated herein contain, each based on its weight, at least one linear saturated 1-alkanol with from about 12 to about 30 carbon atoms in a total amount of from about 1 to about 2.8 wt %, preferably from about 1.2 to about 2.5 wt %, especially preferably from about 1.4 to about 1.7 wt %, wherein at least one 1-alkanol selected from cetyl alcohol, stearyl alcohol and cetyl alcohol/stearyl alcohol mixtures is present in the composition.

As the fourth essential formulation ingredient, the oxidative compositions as contemplated herein contain at least one anionic surfactant selected from alkyl sulfates and alkyl ether sulfates, each having from about 10 to about 20 carbon atoms in the alkyl group and from about 0 to about 16, preferably two to three, glycol ether groups in the molecule, in a total amount of from about 0.05 to about 0.5 wt %, preferably from about 0.1 to about 0.4 wt %, especially preferably from about 0.15 to about 0.3 wt %, extremely preferably from about 0.2 to about 0.25 wt %, each based on the weight of the oxidative composition.

The at least one alkyl sulfate with from about 10 to about 20 carbon atoms in the alkyl group and zero glycol ether groups in the molecule is preferably selected from lauryl sulfate, myristyl sulfate, cetyl sulfate, stearyl sulfate and arachidyl sulfate as well as mixtures of these alkyl sulfates, especially preferably cetyl sulfate, stearyl sulfate, arachidyl sulfate and cetyl sulfate/stearyl sulfate mixtures. The alkyl sulfates here have a negative charge and are present in salt form, preferably as an alkali salt, alkaline earth salt, ammonium, alkyl ammonium, alkanolamine or glucammonium salt, especially preferably as a sodium, potassium, alkanolamine, especially monoethanolamine, trialkylammonium, triethanolamine, 2-amino-1-butanol, 2-amino-2-methyl-1-propanol, 2-amino-2-methyl-1,3-propanediol, 2-amino-2-methyl-1,3-propanediol, 2-amino-2-ethyl-1,3-propanediol and/or tris-(hydroxymethyl)aminomethane salt.

According to the present disclosure, the at least one alkyl sulfate with from about 10 to about 20 carbon atoms in the alkyl group and zero glycol ether groups in the molecule is especially preferably present in the form of the sodium, potassium or magnesium salt. The at least one alkyl sulfate with from about 10 to about 20 carbon atoms in the alkyl group and zero glycol ether groups in the molecule is extremely preferably selected from sodium lauryl sulfate, sodium myristyl sulfate, sodium cetyl sulfate, sodium stearyl sulfate, sodium arachidyl sulfate, potassium lauryl sulfate, potassium myristyl sulfate, potassium cetyl sulfate, potassium stearyl sulfate, potassium arachidyl sulfate and mixtures of these alkyl sulfates. Furthermore, the at least one alkyl sulfate with from about 10 to about 20 carbon atoms in the alkyl group and zero glycol ether groups in the molecule is extremely preferably selected from sodium cetyl sulfate, potassium cetyl sulfate, potassium stearyl sulfate as well as mixtures of these alkyl sulfates.

The at least one alkyl ether sulfate with from about 10 to about 20 carbon atoms in the alkyl group and from about one to about 16 glycol ether groups in the molecule is preferably selected from laureth sulfate, myristeth sulfate, ceteth sulfate, steareth sulfate and arachideth sulfate as well as mixtures of these alkyl ether sulfates. The at least one alkyl ether sulfate with from about 10 to about 20 carbon atoms in the alkyl group and from about one to about 16 glycol ether groups in the molecule is especially preferably selected from ceteth sulfate, steareth sulfate, arachideth sulfate and ceteth sulfate/steareth sulfate mixtures, wherein the alkyl ether sulfates especially preferably have two to three glycol ether groups in the molecule. The alkyl ether sulfates have a negative charge of one and are present in salt form, preferably as alkali, alkaline earth, ammonium, alkyl ammonium, alkanolamine or glucammonium salts, especially preferably as sodium, potassium, alkanolamine, especially monoethanolamine, trialkylammonium, triethanolamine, 2-amino-1-butanol, 2-amino-2-methyl-1-propanol, 2-amino-2-methyl-1,3-propanediol, 2-amino-2-ethyl-1,3-propanediol and/or tris-(hydroxymethyl)aminomethane salts.

Especially preferably as contemplated herein, the at least one alkyl ether sulfate with from about 10 to about 20 carbon atoms in the alkyl group and from about one to about 16, preferably from about two to about three, glycol ether groups in the molecule is present in the form of the sodium, potassium or magnesium salt. The at least one alkyl ether sulfate with from about 10 to about 20 carbon atoms in the alkyl group and from about one to about 16, preferably from about two to about three, glycol ether groups in the molecule is extremely preferably selected from sodium laureth sulfate, sodium myristeth sulfate, sodium ceteth sulfate, sodium steareth sulfate, sodium arachideth sulfate, potassium laureth sulfate, potassium myristeth sulfate, potassium ceteth sulfate, potassium steareth sulfate, potassium arachideth sulfate and mixtures of these alkyl ether sulfates. Furthermore, the at least one alkyl ether sulfate with from about 10 to about 20 carbon atoms in the alkyl group and from about one to about 16, preferably from about two to about three, glycol ether groups in the molecule is extremely preferably selected from sodium laureth-2-sulfate, sodium laureth-3-sulfate, potassium laureth-2-sulfate and potassium laureth-3-sulfate as well as mixtures of these alkyl ether sulfates.

As the fifth essential formulation ingredient, the oxidative compositions as contemplated herein contain dipicolinic acid in an amount of from about 0.02 to about 0.2 wt %, preferably from about 0.03 to about 0.17 wt %, especially preferably from about 0.05 to about 0.13 wt %, extremely preferably from about 0.07 to about 0.1 wt %, each based on the weight of the free dipicolinic acid and the weight of the oxidative composition as contemplated herein. Dipicolinic acid (pyridine-2,6-dicarboxylic acid) serves as a stabilizer for the hydrogen peroxide oxidizing agent.

As the sixth essential formulation ingredient, the oxidative compositions as contemplated herein contain 1-hydroxyethane-1,1-diphosphonic acid in an amount of from about 0.05 to about 0.5 wt %, preferably from about 0.1 to about 0.4 wt %, especially preferably from about 0.18 to about 0.25 wt %, each based on the weight of the free 1-hydroxyethane-1,1-diphosphonic acid and the rate of the oxidative composition as contemplated herein. 1-Hydroxyethane-1,1-diphosphonic acid (etidronic acid) acts as a chelating agent for polyvalent metal ions, in particular for transition metal cations and thereby as a stabilizer for the hydrogen peroxide oxidizing agent.

As the seventh essential formulation ingredient, the oxidative compositions as contemplated herein contain disodium pyrophosphate in an amount of from about 0.02 to about 0.2 wt %, preferably from about 0.05 to about 0.17 wt %, especially preferably from about 0.1 to about 0.13 wt %, each based on the weight of the oxidative composition as contemplated herein.

The oxidative compositions as contemplated herein contain as the additional formulation ingredient benzoic acid or a salt thereof in a total amount of from about 0.02 to about 0.06 wt %, preferably from about 0.03 to about 0.04 wt %, each based on the weight of free benzoic acid and the weight of the oxidative composition as contemplated herein. In an embodiment preferred as contemplated herein, the benzoic acid is present in salt form, preferably as an alkali, alkaline earth, ammonium, alkyl ammonium, alkanolamine or glucammonium salt, especially preferably as sodium, potassium, alkanolamine, in particular monoethanolamine, trialkylammonium, triethanolamine, 2-amino-1-butanol, 2-amino-2-methyl-1-propanol, 2-amino-2-methyl-1,3-propanediol, 2-amino-2-methyl-1,3-propanediol, 2-amino-2-ethyl-1,3-propanediol and/or tris-(hydroxymethyl)aminomethane salt, especially preferably as a sodium and/or potassium salt.

The oxidative compositions as contemplated herein contain as an additional essential formulation ingredient potassium hydroxide in an amount of from about 0.025 to about 0.3 wt %, preferably from about 0.07 to about 0.15 wt %, each based on the weight of the oxidative composition as contemplated herein.

Other essential features of the oxidative composition as contemplated herein include the fact that it contains no phosphoric acid, no salicylic acid, no diethylenetriamine pentaacetic acid, no ethylenediamine tetraacetic acid and no nitrilotriacetic acid or salts of these salts and no phenacetin, no stannates, no cationic surfactants and no oil.

Another essential feature of the oxidative composition as contemplated herein is that it has a pH in the range of from about 2 to about 3.8 preferably in the range of from about 2.5 to about 3.5, especially preferably in the range of from about 2.8 to about 3.3, each measured at about 20° C.

It has surprisingly been found that oxidative compositions not as contemplated herein, stabilized with a mixture of about 0.15 wt % ethylenediamine tetraacetic acid disodium salt and about 0.034 wt % phosphoric acid, instead of the combination as contemplated herein, including of from about 0.02 to about 0.2 wt % dipicolinic acid, from about 0.05 to about 0.5 wt % 1-hydroxyethane-1,1-diphosphonic acid, from about 0.02 to about 0.2 wt % disodium pyrophosphate and from about 0.025 to about 0.3 wt % potassium hydroxide exhibit an increase in pH to about 4.5 from the same initial pH in the range of from about 2 to about 3.8 after storage of a few weeks, which resulted in degradation of the hydrogen peroxide. Additional essential features of the oxidative compositions as contemplated herein include the fact that they contain no phosphoric acid, no salicylic acid, no diethylenetriamine pentaacetic acid, no ethylenediamine tetraacetic acid and no nitrilotriacetic or salts of these acids as well as no phenacetin and no stannates.

Additional essential features of the oxidative compositions as contemplated herein include the fact that they contain no cationic surfactants or any oil.

Examples of oils that are excluded include natural and synthetic hydrocarbons such as mineral oils, paraffin oils, $C_{18}$-$C_{30}$ isoparaffins, in particular isoeicosane, polyisobutenes and polydecenes, also $C_8$-$C_{16}$ isoparaffins such as isodecane, isododecane, isotetradecane and isohexadecane as well as mixtures thereof and 1,3-di-(2-ethylhexyl)cyclohexane. Additional examples of oils excluded as contemplated herein are selected from the benzoic acid esters of linear or branched $C_{8-22}$ alkanols. Other examples of oils excluded as contemplated herein are the fatty alcohols with from about 6 to about 30 carbon atoms, which are unsaturated or branched and saturated or branched and unsaturated. The branched alcohols, for example, 2-hexyldecanol, 2-octyldodecanol, 2-ethylhexyl alcohol and isostearyl alcohol, are frequently also referred to as Guerbet alcohols because they are accessible by the Guerbet reaction. Additional examples of oils excluded as contemplated herein include the unalkoxylated triglycerides (=triple esters of glycerol) of linear or branched, saturated or unsaturated, optionally hydroxylated $C_{8-30}$ fatty acids, in particular the natural oils. Additional examples of oils excluded as contemplated herein are the dicarboxylic acid esters of linear or branched $C_2$-$C_{10}$ alkanols, for example, diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate. Additional examples of oils excluded as contemplated herein are the esters of linear or branched, saturated or unsaturated fatty alcohols with from about 2 to about 30 carbon atoms with linear or branched, saturated or unsaturated fatty acids with from about 2 to about 30 carbon atoms, which may be hydroxylated. These include 2-hexyldecyl stearate, 2-hexyldecyl laurate, isodecyl neopentanoate, isononyl isononanoate, 2-ethylhexyl palmitate and 2-ethylhexyl stearate. Additional examples of oils excluded as contemplated herein are the addition products of one to five propylene oxide units onto monovalent or polyvalent $C_{8-22}$ alkanols, such as octanol, decanol, decanediol, lauryl alcohol, myristyl alcohol and stearyl alcohol e.g., PPG-2 myristyl ether and PPG-3 myristyl ether. Additional examples of oils excluded as contemplated herein are the addition products of at least six ethylene oxide and/or propylene oxide units onto monovalent or polyvalent $C_{3-22}$ alkanols, such as glycerol, butanol, butanediol, myristyl alcohol and stearyl alcohol, which may be esterified, for example, PPG-14 butyl ether, PPG-9 butyl ether, PPG-10 butanediol, PPG-15 stearyl ether and glycereth-7-diisononanoate. Additional example of oils excluded as contemplated herein are the $C_8$-$C_{22}$ fatty alcohol esters of monovalent or polyvalent $C_2$-$C_7$ hydroxycarboxylic acids, in particular the esters of glycolic acid, lactic acid, malic acid, tartaric acid, citric acid and salicylic acid. Additional examples of oils excluded as contemplated herein are the symmetrical, asymmetrical or cyclic esters of carbonic acid with $C_{3-22}$ alkanols, $C_{3-22}$ alkanediols or $C_{3-22}$ alkanetriols, e.g., dicaprylyl carbonate or the esters according to the teaching of DE 19756454A1, in particular glycerol carbonate. Additional examples of oils excluded as contemplated herein are the esters of dimers of unsaturated $C_{12}$-$C_{22}$ fatty acids (dimer fatty acids) with monovalent linear branched or cyclic $C_2$-$C_{18}$ alkanols or with monovalent, linear or branched $C_2$-$C_6$ alkanols. Additional examples of oils excluded as contemplated herein are silicone oils, including, for example, dialkylsiloxanes and alkylarylsiloxanes such as cyclopentasiloxane, cyclohexasiloxane, dimethylpolysiloxane and methylphenyl polysiloxane, but also hexamethyldisiloxane, octamethyltrisiloxane and decamethyltetrasiloxane.

Additional oxidative compositions as contemplated herein are exemplified in that at least one nonionic emulsifier is present in a total amount of from about 0.1 to about 0.4 wt %, preferably from about 0.2 to about 0.35 wt %, each based on the weight of the oxidative composition, wherein this nonionic emulsifier preferably has an HLB value in the range of from about 14 to about 16, especially preferably in the range of from about 14.5 to about 15.5.

A first group of nonionic emulsifiers preferred as contemplated herein are the linear ethoxylated fatty alcohols with from about 12 to about 22 carbon atoms in the alkyl group and a degree of ethoxylation of from about 15 to about 30 mol ethylene oxide, preferably of from about 20 to about 25 mol ethylene oxide. Preferred members of this group are the adducts of from about 15 to about 30 preferably from about 20 to about 25 mol ethylene oxide onto 1 mol lauryl alcohol, tridecyl alcohol, myristyl alcohol, cetyl alcohol, palmitoleyl alcohol, stearyl alcohol, oleyl alcohol, arachyl alcohol and behenyl alcohol as well as their technical grade mixtures. Adduct of from about 15 to about 30, preferably from about 20 to about 25 mol ethylene oxide onto technical grade fatty alcohols with from about 12 to about 18 carbon atoms such as coconut, palm, palm kernel or tallow fatty alcohols are also suitable. Especially preferred nonionic emulsifiers are the $C_{12}$-$C_{18}$ alkanols with from about 15 to about 30 preferably from about 20 to about 25 units ethylene oxide per molecule as well as mixtures of these substances, in particular ceteth-12, ceteth-20, ceteth-30, steareth-12, steareth-20, steareth-30, laureth-12 and beheneth-20 as well as mixtures thereof, in particular ceteth-20, steareth-20 and ceteareth-20.

A second group of nonionic emulsifiers preferred as contemplated herein are the ethoxylated glycerol esters of linear saturated and unsaturated $C_{12}$-$C_{22}$ carboxylic acids which may be hydroxylated, with a degree of ethoxylation of from about 15 to about 60 mol ethylene oxide, preferably from about 20 to about 40 mol ethylene oxide. These ethoxylated glycerol esters preferably originate from myristic acid, palmitic acid, stearic acid, 12-hydroxystearic acid or from mixtures of these fatty acids. Preferred ethoxylated glycerol esters of linear saturated and unsaturated $C_{12}$-$C_{22}$ carboxylic acids, which may be hydroxylated with a degree of ethoxylation of from about 15 to about 60 mol ethylene oxide, are selected from PEG-20 hydrogenated castor oil, PEG-40 hydrogenated castor oil and PEG-60 hydrogenated castor oil, PEG-20 castor oil, PEG-40 castor oil and PEG-60 castor oil, especially preferably PEG-40 castor oil.

In comparison between the two aforementioned nonionic emulsifier classes, the group of linear ethoxylated fatty alcohols with from about 12 to about 22 carbon atoms in the alkyl group and a degree of ethoxylation of from about 15 to about 30 mol ethylene oxide in comparison with the group of ethoxylated glycerol esters of linear saturated and unsaturated $C_{12}$-$C_{22}$ carboxylic acids which may be hydroxylated, with a degree of ethoxylation of from about 15 to about 60 mol ethylene oxide are preferred as contemplated herein. Even better emulsion stabilities can be achieved with the aforementioned linear ethoxylated fatty alcohols than with the ethoxylated glycerol esters.

Additional oxidative compositions preferred as contemplated herein are exemplified in that they contain xanthan, preferably in an amount of from about 0.05 to about 0.4 wt %, preferably from about 0.1 to about 0.3 wt %, each based on the weight of the oxidative composition as contemplated herein.

Additional preferred oxidative compositions as contemplated herein contain, each based on the weight of the oxidative composition:
- at least one linear saturated 1-alkanol with from about 12 to about 30 carbon atoms selected from cetyl alcohol, stearyl alcohol and cetyl alcohol/stearyl alcohol mixtures in a total amount of from about 1 to about 2.8 wt % preferably from about 1.2 to about 2.5 wt %, especially preferably from about 1.4 to about 1.7 wt %,
- additionally at least one anionic surfactant selected from sodium cetyl sulfate, sodium stearyl sulfate, potassium cetyl sulfate, potassium stearyl sulfate as well as mixtures of these alkyl sulfates in a total amount of from about 0.05 to about 0.5 wt %, preferably from about 0.1 to about 0.4 wt %, especially preferably from about 0.15 to about 0.3 wt %, extremely preferably from about 0.2 to about 0.25 wt % and
- additionally at least one nonionic emulsifier, selected from PEG-40 castor oil in a total amount of from about 0.1 to about 0.4 wt %, preferably from about 0.2 to about 0.35 wt %.

Additional oxidative compositions preferably as contemplated herein contain, each based on the weight of the oxidative composition:
- at least one linear saturated 1-alkanol with from about 12 to about 30 carbon atoms, selected from cetyl alcohol, stearyl alcohol and cetyl alcohol/stearyl alcohol mixtures in a total amount of from about 1 to about 2.8 wt % preferably from about 1.2 to about 2.5 wt %, especially preferably from about 1.4 to about 1.7 wt %,
- additionally at least one anionic surfactant selected from sodium cetyl sulfate, sodium stearyl sulfate, potassium cetyl sulfate, potassium stearyl sulfate as well as mixtures of these alkyl sulfates in a total amount of from about 0.05 to about 0.5 wt %, preferably from about 0.1 to about 0.4 wt %, especially preferably from about 0.15 to about 0.3 wt %, extremely preferably from about 0.2 to about 0.25 wt % and
- additionally at least one nonionic emulsifier, selected from ceteth-20, steareth-20 and ceteareth-20 in a total amount of from about 0.1 to about 0.4 wt %, preferably from about 0.2 to about 0.35 wt %.

Additional oxidative compositions as contemplated herein preferably contain, each based on the weight of the oxidative composition:
- at least one linear saturated 1-alkanol with from about 12 to about 30 carbon atoms, selected from cetyl alcohol, stearyl alcohol and cetyl alcohol/stearyl alcohol mixtures in a total amount of from about 1 to about 2.8 wt % preferably from about 1.2 to about 2.5 wt %, especially preferably from about 1.4 to about 1.7 wt %,
- additionally at least one anionic surfactant selected from sodium cetyl sulfate, sodium stearyl sulfate, potassium cetyl sulfate, potassium stearyl sulfate as well as mixtures of these alkyl sulfates in a total amount of from about 0.05 to about 0.5 wt %, preferably from about 0.1 to about 0.4 wt %, especially preferably from about 0.15 to about 0.3 wt %, extremely preferably from about 0.2 to about 0.25 wt %,
- additionally at least one nonionic emulsifier, selected from ceteth-20, steareth-20 and ceteareth-20 in a total amount of from about 0.1 to about 0.4 wt %, preferably from about 0.2 to about 0.35 wt %, and
- additionally from about 0.05 to about 0.4 wt %, preferably from about 0.1 to about 0.3 wt % xanthan.

The oxidative composition as contemplated herein preferably has a viscosity in the range of from about 800 to about 4200 mPas, especially preferably from about 1500 to about 3500 mPas, extremely preferably from about 1800 to about 3000 mPas, each measured at about 20° C. in a Haake viscometer model MV2 at about 8 rpm.

Another subject matter of the present patent application is a kit for oxidative color change of keratin fibers, containing two separate compositions (A) and (B),
wherein
composition (B) contains an inventive oxidative composition or a preferred oxidative composition as contemplated herein as described above, i.e., an oxidative composition containing:
- from about 50 to about 97 wt %, preferably from about 80 to about 95 wt %, especially preferably from about 85 to about 92 wt % water,
- from about 0.5 to about 20 wt % hydrogen peroxide,
- at least one linear saturated 1-alkanol with from about 12 to about 30 carbon atoms in a total amount of from about 1 to about 2.8 wt %, preferably from about 1.2 to about 2.5 wt % especially preferably from about 1.4 to about 1.7 wt %, additionally
- at least one anionic surfactant selected from alkyl sulfates and alkyl ether sulfates, each with from about 10 to about 20 carbon atoms in the alkyl group and from about zero to about 16, preferably from about two to about three glycol ether groups in the molecule in a total amount of from about 0.05 to about 0.5 wt %, preferably of from about 0.1 to about 0.4 wt %, especially preferably from about 0.15 to about 0.3 wt %, extremely preferably from about 0.2 to about 0.25 wt %, additionally
- dipicolinic acid in an amount of from about 0.02 to about 0.2 wt %, preferably from about 0.03 to about 0.17 wt %, especially preferably from about 0.05 to about 0.13 wt %, extremely preferably from about 0.07 to about 0.1 wt %, additionally
- 1-hydroxyethane-1,1-diphosphonic acid in an amount of from about 0.05 to about 0.5 wt %, preferably from about 0.1 to about 0.4 wt %, especially preferably from about 0.18 to about 0.25 wt %, additionally
- disodium pyrophosphate in an amount of from about 0.02 to about 0.2 wt %, preferably from about 0.05 to about 0.17 wt %, especially preferably from about 0.1 to about 0.13 wt %, additionally
- benzoic acid or a salt thereof in a total amount of from about 0.02 to about 0.06 wt %, preferably from about 0.03 to about 0.04 wt %, additionally
- potassium hydroxide in an amount of from about 0.025 to about 0.3 wt %, preferably from about 0.07 to about 0.15 wt %, wherein the oxidative composition has a pH in the range of from about 2 to about 3.8, preferably in the range of from about 2.5 to about 3.5, especially preferably in the range of from about 2.8 to about 3.3, each measured at 20° C.,
wherein it contains no phosphoric acid, no salicylic acid, no diethylenetriamine pentaacetic acid, no ethylenediamine tetraacetic acid and no nitrilotriacetic acid or salts of these acids and no phenacetin, no stannates, no cationic surfactants and no oil, and wherein all the quantitative amounts are based on the weight of the oxidative composition; and the composition (A) contains, each based on the weight of the composition (A), from about 25 to about 90 wt % preferably from about 65 to about 85 wt % water, ammonia and/or monoethanolamine, additionally at least one 1-alkanol with from about 10 to about 30 carbon atoms which is linear or branched and saturated or unsaturated and is preferably selected from lauryl alcohol, myristyl alcohol, cetyl alcohol, stearyl alcohol, arachidyl alcohol, 2-octyldodecan-1-ol and behenyl alcohol as well as mixtures of these 1-alkanols, especially preferably cetyl alcohol, stearyl alcohol, arachidyl alcohol, behenyl alcohol and cetyl alcohol/stearyl alcohol mixtures in a total amount of from about 2 to about 20 wt % preferably from about 2.5 to about 16 wt %, additionally at least one surfactant in a total amount of from about 0.1 to about −7 wt % preferably from about 1.8 to about 4 wt %, and optionally additional ingredients such as organic solvents, chelating agents, antioxidants and/or reducing agent (to improve the stability of the oxidative dye precursors in storage), polymers, oils, silicones and perfumes and optionally at least one oxidative dye precursor and has a pH in the range of from about 8 to about 11.5, measured at about 20° C., wherein the compositions (A) and (B) are preferably present in a weight ratio A/B in the range of from about 0.33 to about 3, especially preferably from about 0.5 to about 2, extremely preferably about 1:1.

Composition (A) corresponds to the alkalizing preparation described above. Composition (A) contains ammonia and/or monoethanolamine as the alkalizing agent plus optionally at least one additional alkalizing agent selected from the group formed from alkanolamines other than monoethanolamine, basic amino acids as well as inorganic alkalizing agents such as alkaline (earth) meal hydroxides, alkaline (earth) metal metasilicates, alkaline (earth) metal phosphates and alkaline (earth) metal hydrogen phosphates. Suitable inorganic alkalizing agents include sodium hydroxide, potassium hydroxide, sodium silicate and sodium metasilicate. Alkanolamines that are different from monoethanolamine and are preferred as contemplated herein are selected from 2-amino-2-methylpropanol and triethanolamine. The basic amino acids that can be used as alkalizing agents as contemplated herein are preferably selected from arginine, lysine, ornithine and histidine, especially preferably arginine.

Ammonia ($NH_3$) is usually used in the form of its aqueous solution. Aqueous ammonia solutions often contain ammonia ($NH_3$) in concentrations of from about 10 to about 32 wt %. Use of an aqueous ammonia solution containing about 25 wt % ammonia ($NH_3$) is preferred here.

The total amount of alkalizing agent is preferably selected so that the mixture, i.e., the ready-to-use color changing agent has an alkaline pH, preferably a pH of from about 8 to about 11.5, especially preferably a pH of from about 8.5 to about 11, extremely preferably a pH of from about 9.0 to about 10.5. Ammonia and/or monoethanolamine are preferably used in the composition (A) used as contemplated herein in amount of from about 0.01 to about 10 wt % preferably from about 0.1 to about 7.5 wt % more preferably from about 0.2 to about 5.5 wt % and especially preferably from about 0.4 to about 4.5 wt %, each based on the weight of the composition (A) so that the pH of the composition (A) is in the range of from about 8 to about 11.5, measured at about 20° C.

The alkalizing composition (A) used as contemplated herein contains as an optional ingredient at least one oxidative dye precursor, preferably selected from one or more developer components and optionally one or more coupler components.

At least one oxidative dye precursor in a total amount of from about 0.0001 to about 10.0 wt %, preferably from about 0.001 to about 8 wt %, each based on the weight of the composition (A), is preferably contained or present.

It may be preferable as contemplated herein to choose as the developer component at least one compound formed from p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine as well as their physiologically safe salts, in particular the hydrochlorides and sulfates and hydrosulfates. At least one developer component is preferably used in a total amount of from about 0.0001 to about 10.0 wt %, preferably from about 0.001 to about 8 wt %, each based on the weight of the composition A.

Coupler components alone in the context of oxidative dying do not form a significant color, but instead they always require the presence of developer components. It is therefore preferable as contemplated herein for at least one coupler component to be used in addition when at least one developer component is used.

Preferred coupler components as contemplated herein are selected from 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol, 2,4-dichloro-3-aminophenol, 2-(2,4-diaminophenoxy)ethanol, 1,3-bis-(2,4-diaminophenoxy)propane, 1-methoxy-2-amino-4-(2-hydroxyethylamino)benzene, 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, resorcinol monomethyl ether, 2-methylresorcinol, 5-methylresorcinol, 2,5-dimethylresorcinol, 2-chlororesorcinol, 4-chlororesorcinol, pyrogallol, 1,2,4-trihydroxybenzene, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6- dihydroxy-4-methylpyridine, 2,6-diaminopyridine, 2,3-diamino-6-methoxypyridine, 3,5-diamino-2,6-dimethoxypyridine, 2,6-dihydroxy-3,4-dimethylpyridine, 3,4-diaminopyridine, 2-(2-methoxyethyl)amino-3-amino-6-methoxypyridine, 2-(4'-methoxyphenyl)amino-3-aminopyridine, 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, 2,3-dihydroxynaphthalene, 4-hydroxyindole, 6-hydroxyindole, 7-hydroxyindole, 4-hydroxyindoline, 6-hydroxyindoline, 7-hydroxyindoline, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine of mixtures of these compounds or their physiologically safe salts.

At least one coupler component is preferably present in a total amount of from about 0.001 to about 10.0 wt %, preferably from about 0.001 to about 8 wt %, each based on the weight of the composition A.

Developer components and coupler components are generally used in approximately equimolar amounts if equimolar use has proven expedient, then a certain excess of individual oxidative dye precursors is not a disadvantage so that the developer components and coupler components may be present in a molar ratio of from about 1:0.5 to about 1:3, in particular from about 1:1 to about 1:2.

Kits preferred as contemplated herein for oxidative color change of keratinic fibers are exemplified in that the aforementioned inventive oxidative composition (B) or preferred oxidative composition (B) as contemplated herein and the aforementioned alkalizing composition (A) are present in a weight ratio A/B of from about 0.33 to about 3, especially preferably from about 0.5 to about 2 and extremely preferably in a weight ratio of about 1:1.

Especially preferred kits as contemplated herein for oxidative color change of keratinic fibers contain the aforementioned inventive oxidative composition (B) or preferred oxidative composition (B) as contemplated herein and the aforementioned alkalizing composition (A) in a weight ratio A/B of from about 0.33 to about 3, especially preferably of from about 0.5 to about 2 and extremely preferably in a weight ratio of about 1:1, wherein the kit does not contain any other components that are added to the ready-to-use color changing mixture, while components for pretreatment or aftertreatment of the keratinic fibers, for example, conditioners or shampoos may also be present in the kit.

With respect to additional preferred embodiments of the kit as contemplated herein, it also holds, mutatis mutandis, that what was said above also applies to the inventive oxidative compositions and preferred oxidative compositions as contemplated herein as well as what was said about the alkalizing compositions (A) used as contemplated herein.

Another subject matter of the present patent application is a method for oxidative color change of keratinic fibers, which is exemplified by the following method steps:

Providing an oxidative composition (B) according to any one of claims 1 to 8 containing, each based on the weight of the oxidative composition:

from about 50 to about 97 wt %, preferably from about 80 to about 95 wt % especially preferably from about 85 to about 92 wt % water, additionally from about 0.5 to about 20 wt % hydrogen peroxide, additionally at least one linear saturated 1-alkanol with from about 12 to about 30 carbon atoms in a total amount of from about 1 to about 2.8 wt % preferably from about 1.2 to about 2.5 wt % especially preferably from about 1.4 to about 1.7 wt %, additionally at least one anionic surfactant selected from alkyl sulfates and alkyl ether sulfates, each with from about 10 to about 20 carbon atoms in the alkyl group and from about zero to about 16, preferably two to three glycol ether groups in the molecule in a total amount of from about 0.05 to about 0.5 wt %, preferably of from about 0.1 to about 0.4 wt %, especially preferably from about 0.15 to about 0.3 wt %, extremely preferably from about 0.2 to about 0.25 wt %, additionally dipicolinic acid in an amount of from about 0.02 to about 0.2 wt %, preferably from about 0.03 to about 0.17 wt %, especially preferably from about 0.05 to about 0.13 wt %, extremely preferably from about 0.07 to about 0.1 wt %, additionally 1-hydroxyethane-1,1-diphosphonic acid in an amount of from about 0.05 to about 0.5 wt %, preferably from about 0.1 to about 0.4 wt %, especially preferably from about 0.18 to about 0.25 wt %, additionally disodium pyrophosphate in an amount of from about 0.02 to about 0.2 wt %, preferably from about 0.05 to about 0.17 wt %, especially preferably from about 0.1 to about 0.13 wt %, additionally benzoic acid or a salt thereof in a total amount of from about 0.02 to about 0.06 wt %, preferably from about 0.03 to about 0.04 wt %, additionally potassium hydroxide in an amount of from about 0.025 to about 0.3 wt %, preferably from about 0.07 to about 0.15 wt %, wherein the oxidative composition has a pH in the range of from about 2 to about 3.8, preferably in the range of from about 2.5 to about 3.5, especially preferably in the range of from about 2.8 to about 3.3, each measured at about 20° C., wherein no phosphoric acid, no salicylic acid, no diethylenetriamine pentaacetic acid, no ethylenediamine tetraacetic acid and no nitrilotriacetic acid or salts of these acids and no phenacetin, no stannates, no cationic surfactants and no oil are present, and providing a composition (A) which contains, based on its weight, from about 25 to about 90 wt % preferably from about 65 to about 85 wt % water, ammonia and/or monoethanolamine, additionally at least one 1-alkanol with from about 10 to about 30 carbon atoms, which is linear or branched and saturated or unsaturated and is preferably selected from lauryl alcohol, myristyl alcohol, cetyl alcohol, stearyl alcohol, arachidyl alcohol, 2-octyldodecan-1-ol and behenyl alcohol as well as mixtures of these 1-alkanols, especially preferably cetyl alcohol, stearyl alcohol, arachidyl alcohol, behenyl alcohol and cetyl alcohol/stearyl alcohol mixtures in a total amount of from about 2 to about 20 wt % preferably from about 2.5 to about 16 wt %, additionally, at least one surfactant in a total amount of from about 0.1 to about 7 wt % preferably from about 1.8 to about 4 wt %, and optionally additional ingredients such as organic solvents, chelating agents, antioxidants and/or reducing agent (to improve the stability of the oxidative dye precursors in storage), polymers, oils, silicones and perfumes, and optionally at least one oxidative dye precursor and has a pH in the range of from about 8 to about 11.5, measured at about 20° C., wherein all the quantitative amounts are based on the weight of the composition A; producing a mixture of the aforementioned oxidative composition (B) and the aforementioned composition A, preferably in a mixing ratio A/B based on the weight in the range of from about 0.33 to about 3, especially preferably from about 0.5 to about 2, extremely preferably about 1:1, then immediately thereafter distributing the ready-to-use agent on the fibers, leaving the agent on the fibers for a period of from about 1 to about 60 minutes, preferably from about 10 to about 45 minutes, especially preferably from about 20 to about 30 minutes, immediately thereafter rinsing the remaining agent out of the fibers and optionally drying the fibers.

Preferred methods for oxidative color change of keratinic fibers as contemplated herein are exemplified in that the aforementioned oxidative composition (B) and the aforementioned alkalizing composition (A) are mixed together in a weight-based mixing ratio A/B in the range of from about 0.33 to about 3, especially preferably from about 0.5 to about 2, extremely preferably about 1:1.

With respect to additional preferred embodiments of the method as contemplated herein, what was said above about the inventive oxidative compositions and the preferred oxidative compositions as contemplated herein as well as the alkalizing compositions (A) used as contemplated herein also applies here, mutatis mutandis.

Keratinic fibers, i.e., fibers containing keratin are to be understood as contemplated herein to be wool, furs, feathers and in particular human hair. However, the coloring and/or lightening methods as contemplated herein may also be used in principle on other natural fibers such as cotton, jute, sisal, linen, silk or modified natural fibers, for example, regenerated cellulose, nitrocellulose, alkyl cellulose or hydroxyalkyl cellulose or acetyl cellulose.

The ready-to-use coloring agent of the method as contemplated herein is preferably prepared by combining the inventive or preferred oxidative composition as contemplated herein with an alkalizing composition (A) used as contemplated herein in a resealable container and then mixing them.

In the subsequent method step, the ready-to-use coloring agent is distributed on the keratinic fibers. In the method for color change of human hair, the ready-to-use agent is distributed directly on the user's head hair. The distribution is preferably performed manually. To do so, the user removes the ready-to-use agent from the mixing container, preferably the resealable container, by scooping or pouring it onto his/her hand and then distributing it and preferably working the agent into the head hair. Direct contact between the ready-to-use color change agent and the user's hands is preferably prevented by using suitable gloves such as disposable gloves made of latex, for example.

Then the ready-to-use coloring agent remains on the fibers to be treated for a period of from about 1 to about 60 minutes. The period of time is preferably in the range of from about 10 to about 45 minutes, especially preferably from about 20 to about 30 minutes.

The use temperatures may be in a range between from about 15 and about 40° C. During the remaining time of the agent on the fibers, a higher or precisely defined temperature may optionally also be set by external heat source. It is especially preferable for the color change to be supported by physical measures. Methods as contemplated herein, in which the application is supported by using heat, IR and/or UV radiation during the treatment time, may be preferred here.

After the end of the treatment time, the ready-to-use coloring agent and/or the remaining coloring agent is removed in the last method step by rinsing it out of the fibers to be treated. To do so, the fibers are rinsed with water and/or an aqueous surfactant preparation. To do so, hot water at from about 20° C. to about 40° C. and/or a suitable thermally regulated aqueous surfactant preparation is generally used. This may optionally be followed by additional treatment steps such as applying a leave-on conditioner or a rinse-off conditioner, another coloring step, for example, dyeing or lightening strands, shaping the hair and/or drying the hair.

Examples

The following examples are presented to illustrate the subject matter of the present disclosure without being limited thereto.

|  | E1 (inventive) | E2 (inventive) | E3 (inventive) | Comparison |
|---|---|---|---|---|
| Cetearyl alcohol | 2.500000 | 1.624000 | 1.700000 | 1.627050 |
| Sodium cetearyl sulfate | 0.300000 | 0.170000 | 0.200000 | 0.157500 |
| Dipicolinic acid | 0.100000 | 0.100000 | 0.100000 | — |
| 1-hydroxyethane-1,1-- diphosphonic acid | 0.186000 | 0.186000 | 0.186000 | — |
| Disodium pyrophosphate | 0.100000 | 0.100000 | 0.100000 | 0.300000 |
| Sodium benzoate | 0.040000 | 0.040000 | 0.040000 | 0.040000 |
| Potassium hydroxide | 0.092500 | 0.092500 | 0.071500 | — |
| Disodium EDTA | — | — | — | 0.150000 |
| Phosphoric acid | — | — | — | 0.034000 |
| Ceteareth-20 | 0.300000 | — | 0.200000 |  |
| PEG-40 castor oil | — | 0.315000 | — | 0.315000 |

-continued

|  | E1 (inventive) | E2 (inventive) | E3 (inventive) | Comparison |
|---|---|---|---|---|
| Hydrogen peroxide | 6.000000 | 6.000000 | 6.000000 | 6.000000 |
| 1,2-Propylene glycol | — | — | 0.600000 | — |
| Xanthan | — | — | 0.300000 | — |
| Demineralized water | 90.381500 | 91.372500 | 90.500000 | 91.376450 |
| pH (20° C.) directly after production | 2.83 | 2.98 | 2.70 | 3.74 |
| pH (20° C.) after 24 weeks at −10° C./20° C./+40° C. | 2.87/2.83/2.82 | 2.98/2.93/2.94 | 2.67/2.63/2.70 | 3.64/4.05/4.44 |
| Emulsion stability after 24 weeks of storage at +40° C. or −10° C. | Yes | Yes | Yes | No |
| Viscosity (mPas) after 24 weeks at −10° C./20° C./+40° C. | Starting viscosity: 2057 2463/1833/2917 | Starting viscosity: 2630 2108/2295/2581 | Starting viscosity: 2961 2619/3068/4094 | Starting viscosity: 2940 X/3650/X |

The oxidative compositions E1, E2 and E3 as contemplated herein presented above as well as the comparative composition (all oil-in-water emulsions) were prepared by the usual methods (separate heating of $H_2O_2$-free water phase and emulsifier- and surfactant-containing fat phase to approx. 85° C. each, then mixing the hot phases and stirring after cooling to approx. 20-30° C., adding stabilizers and $H_2O_2$ and optionally xanthan, then adjusting the pH). Then their viscosity (initial viscosity) and pH were measured. The compositions were then stored for 24 weeks each in the dark at a temperature of −10° C., +20° C. or +40° C. Next the viscosities and the pH levels were measured again.

The oxidative compositions E1, E2 and E3 as contemplated herein remain stable with respect to the starting values for the pH and with respect to the starting values for the viscosity, wherein the deviations from the starting viscosity were all tolerable and suitable for marketing. The comparative composition underwent breaking of the emulsion, i.e., a separation of the external water phase and the dispersed fat phase after 24 weeks of storage under extremely cold temperature (−10° C.) and high temperature (+40° C.). Therefore no final viscosities were determined for the comparative composition. The pH increased significantly in the course of 24 week storage at +20° C. and +40° C.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An oxidative composition for oxidative treatment of hair, comprising
from about 50 to about 97 wt % water, additionally
from about 0.5 to about 20 wt % hydrogen peroxide, additionally
at least linear saturated 1-alkanol with from about 12 to about 30 carbon atoms in a total amount of from about 1 to about 2.8 wt %, additionally
comprising at least one anionic surfactant selected from alkyl sulfates and alkyl ether sulfates, each with from about 10 to about 20 carbon atoms in the alkyl group and from about 0 to about 16 glycol ether groups, additionally
dipicolinic acid in an amount of from about 0.02 to about 0.2 wt %, additionally
1-hydroxyethane-1,1-diphosphonic acid in an amount of from about 0.05 to about 0.5 wt %, additionally
disodium pyrophosphate in an amount of from about 0.02 to about 0.2 wt %, additionally
benzoic acid or a salt thereof in a total amount of from about 0.02 to about 0.06 wt %, additionally
potassium hydroxide in an amount of from about 0.025 to about 0.3 wt %,
wherein the oxidative composition has a pH in the range of from about 2 to about 3.8, each measured at 20° C.,
wherein the composition comprises no phosphoric acid, no salicylic acid, no diethylenetriamine pentaacetic acid, no ethylenediamine tetraacetic acid, no nitrilotriacetic acid or salts of these acids and no phenacetin, no stannates, no cationic surfactants and no oil, and
wherein all the quantity data is based on the weight of the oxidative composition.

2. The composition according to claim 1, wherein at least one linear saturated 1-alkanol with from about 12 to about 30 carbon atoms is selected from lauryl alcohol, myristyl alcohol, cetyl alcohol, stearyl alcohol, arachidyl alcohol, behenyl alcohol, or mixtures thereof.

3. The composition according to claim 1, wherein the at least one alkyl sulfate with from about 10 to about 20 carbon atoms in the alkyl group and zero glycol ether groups in the molecule is selected from sodium cetyl sulfate, sodium stearyl sulfate, potassium cetyl sulfate, potassium stearyl sulfate, or mixtures thereof.

4. The composition according to claim 1, wherein the at least one alkyl ether sulfate with from about 10 to about 20 carbon atoms in the alkyl group and from about one to about 16 glycol ether groups in the molecule is selected from sodium laureth-2-sulfate, sodium laureth-3-sulfate, potassium laureth-2-sulfate, potassium laureth-3-sulfate, or mixtures thereof.

5. The composition according to claim 1, further comprising at least one nonionic emulsifier is present in a total amount of from about 0.1 to about 0.4 wt %.

6. The composition according to claim 5, wherein the at least one nonionic emulsifier is selected from linear ethoxylated fatty alcohols with from about 12 to about 22 carbon atoms in the alkyl group and a degree of ethoxylation of from about 15 to about 30 mol ethylene oxide; or ethoxylated glycerol esters of linear saturated and unsaturated $C_{12}$-$C_{22}$ carboxylic acids which may be hydroxylated, with a degree of ethoxylation of from about 15 to about 60 mol ethylene oxide.

7. The composition according to claim 1, further comprising xanthan.

8. A kit for oxidative color change of keratinic fibers comprising two separate compositions (A) and (B), wherein
composition (B) is an oxidative composition according to claim 1 and composition (A) comprises, based on its weight
from about 25 to about 90 wt % water,
ammonia and/or monoethanolamine,
additionally at least one 1-alkanol with from about 10 to about 30 carbon atoms which is linear or branched and saturated or unsaturated,
in addition at least one surfactant in a total amount of from about 0.1 to about 7 wt %,
and optionally additional ingredients selected from organic solvents, chelating agents, antioxidants and/or reducing agent, polymers, oils, silicones, and perfumes and
optionally at least one oxidative dye precursor,
and has a pH in the range of from about 8 to about 11.5, measured at 20° C.,
wherein all the quantitative amounts are based on the weight of composition A;
wherein compositions (A) and (B) are used in a weight ratio AB in the range of 0.33-3.

9. A method for oxidative color change of keratinic fibers, characterized by
the following method steps:
providing an oxidative composition (B) according to claim 1, comprising
from about 50 to about 97 wt % water, additionally
from about 0.5 to about 20 wt % hydrogen peroxide, additionally
at least linear saturated 1-alkanol with from about 12 to about 30 carbon atoms in a total amount of from about 1 to about 2.8 wt %, additionally
comprising at least one anionic surfactant selected from alkyl sulfates and alkyl ether sulfates, each with from about 10 to about 20 carbon atoms in the alkyl group and from about 0 to about 16 glycol ether groups, additionally
dipicolinic acid in an amount of from about 0.02 to about 0.2 wt %, additionally
1-hydroxyethane-1,1-diphosphonic acid in an amount of from about 0.05 to about 0.5 wt %, additionally
disodium pyrophosphate in an amount of from about 0.02 to about 0.2 wt %, additionally
benzoic acid or a salt thereof in a total amount of from about 0.02 to about 0.06 wt %, additionally
potassium hydroxide in an amount of from about 0.025 to about 0.3 wt %,
wherein the oxidative composition has a pH in the range of from about 2 to about 3.8, each measured at 20° C.,
wherein the composition comprises no phosphoric acid, no salicylic acid, no diethylenetriamine pentaacetic acid, no ethylenediamine tetraacetic acid, no nitrilotriacetic acid or salts of these acids and no phenacetin, no stannates, no cationic surfactants and no oil, and
providing a composition (A) comprising, based on its weight,
from about 25 to about 90 wt % water,
ammonia and/or monoethanolamine,
additionally, at least one 1-alkanol with 1 from about 0 to about 30 carbon atoms which is linear or branched and saturated or unsaturated,
additionally, at least one surfactant in a total amount of from about 0.1 to about 7 wt %,
and optionally additional ingredients selected from organic solvents, chelating agents, antioxidants and/or reducing agent, polymers, oils, silicones, and perfumes and
optionally at least one oxidative dye precursor;
and has a pH in the range of from about 8 to about 11.5, measured at 20° C.,
wherein all the quantitative amounts are based on the weight of composition A;
preparing a mixture of the aforementioned oxidative composition (B) and the aforementioned composition (A) in a weight-based mixing ratio AB in the range of from about 0.33 to about 3, immediately thereafter distributing the ready-to-use composition on the fibers, leaving the composition on the fibers for a period of from about 1 to about 60 minutes, immediately thereafter rinsing the remaining composition out of the fibers and optionally drying the fibers.

* * * * *